United States Patent [19]
Gray et al.

[11] Patent Number: 6,008,405
[45] Date of Patent: Dec. 28, 1999

[54] STABILIZED PERACID SOLUTIONS

[75] Inventors: Andrew Kevin Gray, Widnes; Alun Pryce James, Liverpool, both of United Kingdom

[73] Assignee: Solvay Interox Limited, United Kingdom

[21] Appl. No.: 09/041,036

[22] Filed: Mar. 12, 1998

[30] Foreign Application Priority Data

Mar. 15, 1997 [GB] United Kingdom .................... 9705448

[51] Int. Cl.$^6$ ..................................................... Z07C 409/24
[52] U.S. Cl. ..................................................................... 562/3
[58] Field of Search ..................................................... 562/3

[56] References Cited

U.S. PATENT DOCUMENTS 2,347,434  4/1944  Reichert et al. .
2,590,856  4/1952  Greenspan et al. .
2,609,391  9/1952  Greenspan et al. .

FOREIGN PATENT DOCUMENTS 0 563 584   2/1993  European Pat. Off. .
925 373     5/1960  United Kingdom .
91/07375    5/1991  WIPO .
91/13058    9/1991  WIPO .

*Primary Examiner*—Gary Geist
*Assistant Examiner*—Brian J. Davis
*Attorney, Agent, or Firm*—Larson & Taylor

[57] ABSTRACT

The current invention relates to the stabilisation of peroxyacid solutions. There is provided a tin based stabiliser composition obtained by the ageing of an alkaline solution of a tin compound and a phosphorus containing compound. The stabiliser is particularly suitable for the stabilisation of non-equilibrium solutions of peroxyacids.

26 Claims, No Drawings

STABILIZED PERACID SOLUTIONS

BACKGROUND OF THE INVENTION

This invention concerns stabilised aqueous peracid solutions, and processes for the preparation of such solutions. The invention particularly concerns stabilised solutions of aliphatic peracids, especially peracetic acid solutions.

Aqueous solutions of peracids have numerous applications in industry, including particularly use as bleaching agents, reagents in chemical synthesis, and especially as disinfectants for domestic, industrial and environmental applications. Many of these applications are carried out at locations removed from the location at which the peracid is produced, and thus the peracids are advantageously stable at the very least during transport to the application site. In a very large number of cases, the peracid can also be stored, for example in warehouses, for a significant period, often in the region of months or even years, prior to use.

The stability of peracid solutions can be improved by the avoidance of the introduction into the solution during its manufacture of impurities which can destabilise the peracid, notably transition metal ions. However, as a practical matter it is virtually impossible to ensure that no such impurities are present. Furthermore, even if impurities are avoided during manufacture, there remains the possibility that impurities may be introduced during any subsequent packaging or transportation of the solution. It is therefore desirable that the peracid solutions are stabilised against decomposition by such impurities. In addition to stabilising the peracid solution during storage, the presence of stabilisers in the peracid solution may also have the additional benefit of enhancing the stability of the peracid solution in use, and consequently increasing the efficacy of the solution. The presence of stabilisers can also reduce the hazardous properties of the solution.

Many systems have been proposed for use as stabilisers for peracid solutions. Amongst those which have found wide application include dipicolinic acid, for example as disclosed in U.S. Pat. No. 2,609,391. Other compounds include phosphonates, notably those disclosed in British Patent No. 925,373 Henkel. In some instances, combinations of stabilisers are employed, for example the combinations of dipicolinic acid and phosphonates disclosed in International application publication numbers. WO91/07375 and WO91/13058. Phosphates have been proposed for use as stabilicers for peracid solutions in U.S. Pat. Nos. 2,347,434 and 2,590,856. European Patent No. 0 563 584 teaches that stannates can be employed to stabilise peracid solutions provided the stannate is added to the peracid solution during or after manufacture, or is added to the reaction mixture immediately before the reaction commences. The stannate can be employed in the peracid solution in conjunction with a separately added co-stabiliser, and although a large number of potential co-stabilisers, including poly and pyrophosphoric acids and their salts are contemplated, only dipicolinic acid and 1-hydroxyethane-1,1-diphosphonic acid are exemplified. European Patent No. 0 563 584 therefore contains no teaching on the use of a stannate derivatives stabiliser for stabilising peracid solutions, nor any indication that the preparation of the stabiliser system is of any importance.

Although some stabiliser systems for peracid solutions are already known, it remains desirable to identify additional or further systems.

It is a first object of certain aspects of the present invention to provide an additional or further stabiliser system for aqueous peracid solutions.

It is a second object of further aspects of the present invention to provide a process for the production of stabilised aqueous peracid solutions.

It is a third object of yet further aspects of the invention to provide a stabiliser system which will increase the time period required for attainment of equilibrium of peracid solutions, where the peracid is present in excess of its equilibrium concentration.

BRIEF SUMMARY OF THE INVENTION

According to one aspect of the invention there is provided a process for the stabilisation of an aqueous solution of a peroxyacid by means of the addition of an effective amount of a tin based stabiliser thereto, or to one or more components of that solution, characterised in that said stabiliser is prepared by introducing a tin compound and a phosphorus containing compound into an alkaline solution thereby forming a coloured solution, which is then stored for a time sufficient to obtain its fading before introduction into the peroxyacid solution or a component thereof.

According to a further aspect of the present invention, there is provided an aqueous solution of a peracid comprising a tin based stabiliser, characterised in that the tin based stabiliser is obtainable by a process comprising:

a) preparing a solution containing a water soluble salt of a stannate and one or more water soluble phosphorus containing salts.

b) adjusting the pH of the solution to a pH in the range of 9 to 11.5, thereby forming a yellow solution c) ageing the solution, optionally at elevated temperature, until the yellow coloration fades.

Herein, the term fading does not require the solution to be colourless after the ageing process, but that a detectable decrease in intensity has occurred.

According to a third aspect of the present invention, there is provided a process for the stabilisation of an aqueous solution of a peracid with a tin based stabiliser, characterised in that the process comprises introducing into the peracid solution, or forming the peracid in the presence of a tin based stabiliser obtainable by a process comprising:

a) preparing a solution containing a water soluble salt of a stannate with one or more water soluble phosphorus containing salts b) adjusting the pH of the solution to a pH in the range of 9 to 11.5, thereby forming a yellow solution c) ageing the solution, optionally at elevated temperature, until the yellow coloration fades.

DETAILED DESCRIPTION OF PREFERRED EMBODIMENTS

Peracids which can be stabilized in solution include those derived from mineral acids such as Caro's acid. Preferable, however, are percarboxylic acids where the $pK_a$ of the percarboxylic group in aqueous solution is between 6 and 9. Examples of such peracids include low molecular weight aliphatic peroxyacids, containing up to 6 carbon atoms, of which especially preferred examples comprise peracetic acid and perpropionic acid. Other examples include performic acid, perbutyric acid, dipersuccinic acid, diperglutaric acid, and diperadipic acid. The alkyl part of the chain may be optionally substituted with one-or more substituents selected from halo-, nitro-, amido-, hydroxy-, carboxy-, sulpho-, or phosphono-groups. Contemplated from this group are monochloroperacetic acid, dichloroperacetic acid, trichloroperacetic acid, and trifluoroperacetic acid. Further examples include the monoperacids of dibasic carboxylic acids such as monopersuccinic acid, monoperglutaric acid, monoperadipic acid, and also percitric acid and pertartaric acid. Additionally the substituent may be further derivatised to give groups such as esters or ethers. Examples of these are monoester peracids of formula:

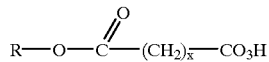

where R represents an alkyl group having from 1 to 4 carbons and x is from 1 to 4.

A mixture of peracids, particularly a mixture of mono- and di-, persuccinic, perglutaric and peradipic acids, may be employed if desired. Especially suitable are the monoester peracids given above, and more especially, mixtures of these comprising x=2, 3, and 4. The compositions may alternatively or additionally include aromatic and substituted aromatic peroxyacids, such as monoperphthalic acid or salts thereof, sulphoperbenzoic acid or salts thereof chloroperbenzoic acids, and tolueneperbenzoic acids.

Additionally, one or more higher molecular weight aliphatic peroxyacids having 6–18 carbon atoms may be employed in combination with the low molecular weight aliphatic peracids given above, although it is recognised that these higher molecular weight aliphatic peroxyacids might not be totally soluble in the stabilised solution. Particularly suitable higher molecular weight acids are linear aliphatic monoperoxy- fatty acids, or monperoxy- or diperoxydicarboxylic acids. Examples of this are peroxyoctanoic acid, peroxydecanoic acid, monoperoxy- or diperoxyazelaic acid, monoperoxy- or diperoxysebacic acid, and monoperoxy- or diperoxydodecanedioic acid.

The peracid, which in fact may be a mixture of peracids, can be present in a wide range of concentrations, for example up to 40%, often up to 15% and more often up to 10%. For any component, % herein is by weight based on the total weight of the composition, unless specifically stated otherwise. The lower limit for the concentration of the peracid is at the discretion of the user, but is normally not below 0.001%. The invention is particularly applicable to ready to use compositions containing a low concentration of peracid, including for example compositions intended for application for cleansing and/or disinfecting purposes to hard surfaces and particularly to non-horizontal surfaces. Such dilute compositions typically contain not less than 0.05%, often not less than 0.1% and more often, not less than 0.5%, and often not more than 5%, more often not more than 2% of peracid. For example in a number of practical embodiments the peracid content is from 0.2%, and often from 0.5%, to 1.5%. It will be recognised that such compositions may contain a significant concentration of hydrogen peroxide, which may, for example, comprise from 1 to 15% of the composition. and in a number of embodiments from 3 to 10%.

Peracid compositions suitable for stabilization according to the present invention, and particularly those containing aliphatic peracids, are often conveniently derived by oxidation of the corresponding aliphatic carboxylic acid with aqueous hydrogen peroxide, optionally in the presence of a strong acid catalyst, and often contain residual amounts of both the carboxylic acid and hydrogen peroxide.

In one aspect of the invention, the solutions to be stabilized comprise the so-called equilibrium peroxycarboxylic acids such as peracetic acid with a content of 0.05 to 40% peracetic acid, preferably 4 to 20% peracetic acid: 5 to 40% acetic acid; 1 to 30% hydrogen peroxide, and the rest being water. Optionally, the solutions contain sufficient mineral acid, such as sulphuric acid, to accelerate the attainment of equilibrium.

Such compositions in many instances contain up to 40% of the corresponding carboxylic acid and up to 30% hydrogen peroxide, with a minimum water content usually of 20%. However, in dilute peracid solutions, the concentration of the carboxylic acid and of hydrogen peroxide each tend to be selected in the range from 0.1% to 12%. The total concentration of carboxylic acid plus percarboxylic acid is often from 0.1 to 50%. It is often convenient to restrict the concentration of hydrogen peroxide to no greater than 7%.

One way of defining such systems is in terms of the equilibrium constant, K. This can be conveniently represented as follows for the current system:

For which:

$$K = \frac{[\text{Peracetic Acid}][\text{Water}]}{[\text{Hydrogen Peroxide}][\text{Acetic Acid}]}$$

Peracetic acid is here being used as representative of peracids in general, for each of which the corresponding equation is valid.

It will be recognized that if two initially identical non-equilibrium compositions have, at the end of a storage period in which equilibration occurs, different equilibrium constants, then the one with the higher equilibrium constant, will have the higher peracetic acid content, and that which caused the improvement will have retarded equilibration.

In another aspect of the invention, the solutions to be stabilized are non-equilibrium solutions of percarboxylic acids such as peracetic acid. Examples of these, are those derived from distillation of a peracetic acid solution, and will usually contain only low amounts of acetic acid or hydrogen peroxide. It is recognised that use of such compositions is desirable and often necessary where for example, acetic acid can cause unnecessary side reactions. The removal further downstream in a process is often required on environmental and economic grounds and also to slow down the growth of micro-organisms which can foul pipes. For the above reasons the use of such non-equilibrium solutions can be especially useful in applications such as pulp delignification, and also in disinfection, particularly in the horticultural industry as well as hard surface cleaners.

Because however, they are non-equilibrium solutions, then once formed, they will rapidly start to revert to the equilibrium composition. Stabilization of these non-equilibrium peracids will obviously mean that the rate of re-equilibration, and hence reduction in the concentration of peracetic acid, is reduced. Although the process cannot be stopped completely, certain factors such as low temperature are known to slow it down. Such compositions typically contain up to 55% of peracetic acid with a small amount of hydrogen peroxide and acetic acid, the rest being water. In a number of other embodiments, the peracetic acid solution is further diluted with water to give solutions containing 20–40% of peracetic acid.

In a yet further aspect the solutions to be stabilised are those non-equilibrium solutions where the peracid is present in an amount in excess of that which would be present were equilibrium to be achieved. These can include so-called in-use compositions where the equilibrium or non-equilibrium solutions described in the previous aspects of the invention are diluted with one or more of the non-peracid components, most often with water. Such compositions will often have a peracid concentration of up to 2%, although the concentration is usually from about 0.001% to about 1%, preferably from about 0.002% to about 0.75%. These can also include compositions which have been cooled for a period prior to use, for example during transport or storage on-site. As the equilibrium constant for peracetic acid solutions is inversely proportional to the temperature, the cooled compositions will have a higher peracetic acid content than the warmer ones, to an extent dependent upon the progress of the composition towards the new equilibrium.

The tin based stabilizer can be obtained in solution via a number of routes. In one method, as part of step a), stannic oxide is dissolved in an alkaline solution. The alkaline solution can be produced from the addition of water to a number of compounds such as NaOH, KOH, $Na_2CO_3$, $(NH_4)_2CO_3$, $NaHCO_3$, $NR_4OH$ and one or more of the other components of step a).

In another method, as part of step a), a soluble stannate salt, or mixture of such salts, such as sodium stannate, potassium stannate, or ammonium stannate is dissolved in water or an aqueous solution of one or more of the other components in step a). In a preferred option, sodium stannate or potassium ztanrnate is employed as the source of tin. In a more preferred method, the source of tin is potassium stannate.

An often preferred further component of the stabilizer system is the soluble salt of a phosphate. The phosphate salt can take the form of the simple monomeric species, or of the condensed linear polyphosphate, or cyclic polyphosphate (metaphosphate). The monomeric phosphate salts are of the general formula, $M_nH_qPO_4$, (in which q=0, 1, or 2; n=1, 2, or 3; n+q=3). Here M can be one or more monovalent cations selected from the following: Li, Na, K, $NH_4$, $NR_4$ (where R represents an alkyl chain containing 1 to 5 C atoms). The polyphosphates have the general formula, $M_{n+2}P_nO_{3n+1}$ where n=2 to 8, and M can be chosen from Li, Na, K, $NH_4$, $NR_4$(where R represents an alkyl chain containing 1 to 5 C atoms). The cyclic polyphosphates have the general formula $M_nP_nO_{3n}$, where N=3 to 8 and M can be chosen from Li, Na, K, $NH_4$, $NR_4$(where R represents a linear or branched alkyl group containing 1 to 5 C atoms).

The above may be optionally introduced into the stabilizer system in their acid form.

Also to be contemplated as phosphorus containing salts are organophosphonates which may be introduced as a soluble salt or more preferably as the parent acid. Compounds which may be contemplated include, ethylphosphonic acid, propylphosphonic acid, butylphosphonic acid, t-butylphosphonic acid, or phenylphosphonic acid. Additionally the phosphonic acid molecules can contain other functional groups such as hydroxy or amino. These are exemplified in compounds such; as 1-hydroxyethylidene-1, 1-diphosphonic acid, and poly(methyleneamino) phosphonic acids such as amino(trimethylene phosphonic acid), and diethylenetriaminepenta(methylenephosphonic acid). Those marketed under the names CIX™, DEQUEST™, BRIQUEST™, TURPINAL™, and SEQUION™ are also employable.

Further additives which may be contemplated are sulphuric acid, or soluble salts thereof. Organosulphonic acids such as decylsulphonic acid, dodecylsulphonic acid, toluenesulphonic acid, as well as their salts, may also be introduced.

Stannate is usually employed at a concentration of up to 15% of the total stabilizer solution, more preferably at a concentration of between 8 to 12%.

The other phosphorus containing additives are typically added at a total concentration of up to 18% with respect to the total weight of the stabilizer solution. More preferably a ccncentration between 10 to 14% is employed.

In step b), the pH is adjusted, often using one or more of the components identified for use in step a). This is carried out until the pH has a value of between 9 and 11.5, more preferably to between 10.5 and 11.5, and most preferably to between 10.9 and 11.1. It will be recognized that the pH can be controlled to a great extent depending on whether or not the acid or the salt form of the above additives is employed.

After addition of all the components in step b), the solution is normally clear, with a yellow coloration. A certain amount of undissolved suspended solid may be present without impairment of the effectiveness of the stabilizer. Before use the solution is allowed to age, during which time its colour fades, preferably to the extent that the resulting stabilizer solution is usually a clear transparent liquid.

In step c), ageing can be carried out either at ambient temperature or optionally at elevated temperature. The minimum period of time for the ageing can be determined by the formula:

$$\text{Time}=y(2.3^{(100-T)/10})$$

where: time is given in hours y is at least 0.1

T is the temperature at which the solution is aged, in Celcius. The value of y can be as low as 0.1, but is more preferably 0.2.

Although in many embodiments of the present invention, the solution obtained by following steps a) and b) as described herein has a readily discernable colouration, in other embodiments it does not have a colouration that is discernable readily to the eye. It is recognised that for such solutions the duration of step c) is not determined by a discernable fading of the colour, but is determined by calculation, and in particular by the formula given above. The maximum period of ageing is at the discretion of the user, irrespective of whether the solution obtained in staep b) is coloured. Usually, y is not greater than 2, often not greater than 1 and in many instances is not greater than 0.5. A preferred range for y is from 0.2 to 0.5.

Accordingly, in some embodiments of the present invention there is provided a process for the stabilisation of an aqueous solution of a peroxyacid by means of the addition of an effective amount of a tin based stabiliser thereto, or to one or more components of that solution, characterised in that the stabiliser is prepared according to the following steps of:

a) preparing a solution containing a water soluble salt of a stannate with one or more water soluble phosphorus containing salts.

b) adjusting the pH of the solution to a pH in the range of 9 to 11.5, c) ageing the solution, optionally at elevated temperature for a period determined by the formula $\text{Time}=y(2.3^{(100-T)/10})$ In which time is given in hours, y is in the range of from 0.1 to 2 and T is the temperature at which the solution is aged, in Celcius.

For ambient, or near-ambient temperatures, the period of ageing is often selected to be between 1 and 3 weeks, whereas at temperatures near the boiling point of the solution it is substantially less. For example at 90° C., an acceptable period is often not longer than 2 hours, and preferably between 30 minutes and 2 hours. As the temperature used does not affect the quality of the stabilizer, it will be recognized that a decision on which temperature is to be used is governed by considerations such as equipment availability, urgency of need for stabilizer and is at the discretion of the user of the invention.

The water to be used for the preparation of the stabiliser solution can be that obtained from the local municipal supply. More preferably the water is further purified such that its conductivity is reduced to below 1 μS/cm. For certain applications, ultra high purity water can be employed with a conductivity of below 0,06 μS/cm.

The use of the tin based stabiliser system herein does not preclude or restrict the presence of other known stabilisers for peroxygens. The tin based stabiliser system may be employed in conjunction with one or more compounds which can be present at concentrations of from 0.001% to 1%. Compounds such as polycarboxylic acids, including for example dipicolinic acid, ethylenediaminetetraacetic acid or citric acid, soluble salts of phosphates which may take the form of simple monomeric species, or of condensed linear polyphosphates or cyclic metaphosphates. Further known stabilisers which may be included are organophosphonates, which molecules may additionally contain other functional groups such as hydroxy or amino. These are exemplified in compounds such as 1-hydroxyethylidene-1,1-diphosphonic acid and poly(methyleneamino)-phosphonic acids such as amino(trimethylenephosphonic acid), and diethylenetriaminepenta (methylenephosphonic acid). Those marketed under the names CIX™, DEQUEST™, BRIQUEST™, TURPINAL™, and SEQUION™ are also employable.

Yet further stabilisers to be contemplated are free radical scavengers. In general these scavengers are selected from amongst phenols, polyols, or thiols. Particularly suitable are those selected from phenols which satisfy the general formula (I)

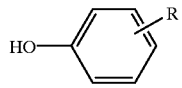

in which R represents at least one substituent selected from alkyl, ether, hydroxyl, carboxylic acid, and aliphatic carboxylic acid ester groups. Normally R in (I), represents from 1 to 4 substituents. One suitable sub-class of phenolic scavengers polyhydroxybenzoic acid or alkyl ester derivatives thereof, the benzene nucleus optionally being further substituted by one or more alkyl substituents. Normally not more than a single carboxylic acid/ester substituent is present. Included within that sub-class are the dihydroxybenzoic acids, gallic acid, pyrogallic acid and ester derivatives thereof. Other suitable sub-classes comprise polyhydroxyalkylbenzenes or ether derivatives thereof. Representatives of that subgroup include alkylresorcinols and alkylhydroquinones. Further suitable radical scavengers are substituted polyaryl compounds including those where one or more of the aryl rings is substituted with a heteroatom. A suitable example from this group is 8-hydroxyquinoline.

According to a yet further aspect of the invention, there is provided a stabiliser which is suitable for stabilisation of peroxyacid solution, characterised in that the stabiliser is a tin based stabiliser as described herein.

Having described the invention in general terms, specific embodiments thereof are described in greater detail by way of example only.

PREPARATION METHOD 1

Potassium stannate(124.73 g), was added to 1 litre of demineralised water of conductivity less than 1 μS/cm), and mixed for 15 minutes. Tetrapotassium pyrophosphate (106.02 g), was then added, and mixed in over 15 minutes. Orthophosphoric acid(90%)(49.89 g) was then added and the solution mixed for a further 45 minutes. The pH was adjusted to pH11±0.1 by the addition of potassium stannate. Half of the solution was kept as such(non-aged), and the other half aged, by heating to 90° C. for a period of 90 minutes.

EXAMPLE 1 AND COMPARISON 1

Hydrogen peroxide(59.7 g at 34.8%), acetic acid(13.8 g), and demineralised water(26.4 g), were mixed together. The non-aged sample(not according to the invention) and the aged sample(according to the invention) of Preparation Method 1, were then added at a concentration of 0.1% with respect to the total weight of the above components, and the system left to equilibrate at ambient temperature. After 9 weeks, the equilibrium constant for the comparison containing non-aged additive was 1.59, and that for the invention mixture containing the aged additive, 1.86. Thus, the peracid content of the solution containing the aged stabilizer of Example 1 was higher than that containing the non-aged sample of Comparison 1.

EXAMPLE 2 AND COMPARISON 2

Hydrogen peroxide(58.3 g at 34.8%), acetic acid(14.2 g), and demineralised water(27.6 g), were mixed together. The non-aged samples(not according to the invention) and the aged sample(according to the invention) of Preparation Method 1, were then added at a concentration of 1.0% with respect to the total weight of the above components, and the system left to equilibrate at ambient temperature. After 9 weeks, the equilibrium constant for the comparison containing non-aged additive was 1.66, and that for the invention mixture containing the aged additive, 1.79. Thus, the peracid content of the solution containing the aged stabilizer of Example 2 was higher than that containing the non-aged sample of Comparison 2.

EXAMPLE 3 AND COMPARISON 3

Hydrogen peroxide(58.3 g at 34.8%), acetic acid(14.1 g), and demineralised water(27.7 g), were mixed together. The non-aged samples(not according to the invention) and the aged samples(according to the invention) of Preparation Method 1, were then added at a concentration of 0.1% with respect to the total weight of the above components, and the system left to equilibrate at 32° C. After 9 weeks, the equilibrium constant for the comparison containing non-aged additive was 1.53, and that for the invention mixture containing the aged additive, 1.77. Thus, the peracid content of the solution containing the aged stabilizer of Example 3 was higher than that containing the non-aged sample of Comparison 3.

EXAMPLE 4 AND COMPARISON 4

Hydrogen peroxide(59.5 g at 34.8%), acetic acid(13.9 g), and demineralised water(26.7 g), were mixed together. The non-aged samples(not according to the invention) and the aged sample(according to the invention) of Preparation Method 1, were then added at a concentration of 1.0% with respect to the total weight of the above components, and the system left to equilibrate at 32° C. After 9 weeks, the equilibrium constant for the comparison containing non-aged additive was 1.68, and that for the invention mixture containing the aged additive, 1.78. Thus, the peracid content of the solution containing the aged stabilizer of Example 4 was higher than that containing the non-aged sample of Comparison 4.

EXAMPLE PREPARATION METHOD 2

To demineralised water(224.37 g), was added potassium stannate(33.60 g), tetrapotassium pyrophosphate(27.09 g), and orthophosphoric acid(13.44 g of an 88% solution). These formed, on dissolution, a clear slightly yellow solution. The pH of the solution was measured, and adjusted to pH 11.0 with further potassium stannate. The solution was then heated to 90° C. for a period of one hour, during which time the solution became colourless. After cooling, the mass of the solution was made up to 300 g by the addition of demineralised water. This gave a solution of about 25% active stabilizer/solids

COMPARISON PREPARATION 2

To demineralised water(7.5164 g), was added potassium stannate(1.1283 g), tetrapotassium pyrophosphate(0.9332 g), and orthophosphoric acid(0.498 g of an 88% solution). These formed, on dissolution, a clear slightly yellow solution. The pH of the solution was measured, and adjusted to pH 11.0 with further potassium stannate. The mass of the solution was then made up to 300 g by the addition of demineralised water.

EXAMPLE 5

To an aqueous solution(99.8873 g) containing 35.29% of peracetic acid and 1.77% of hydrogen peroxide, was added, with stirring, solution(0.1245 g) from Example Preparation Method 2, according to the current invention. This gives a solution of about 300 ppm of active stabilizer/solids.

At ambient temperature, the solution lost 35.3% of the initial peracetic acid over two weeks at ambient temperature.

The unstabilised peracetic acid lost 44 3% of its initial peracetic acid during the same period.

COMPARISON 6

To an aqueous solution(99.8864 g) containing 35.29% of peracetic acid and 1.77% of hydrogen peroxide, was added, with stirring, solution(0.1203 g) from Comparison Preparation 2, not according to the current invention. This gave a solution of about 300 ppm solids.

At ambient temperature, the solution lost 43.4% of the initial peracetic acid over two weeks at ambient temperature.

The unstabilised peracetic acid lost 44.3% of its initial peracetic acid during the same period. This demonstrates that the addition of the stannate and phosphate without ageing did not significantly improve the stability of the peracetic acid solution.

EXAMPLE 7

To an aqueous solution(100 g) containing 34.3% of peracetic acid and 0.9% of hydrogen peroxide, was added the following:

Solution A: Sodium stannate(300 ppm); (Comparison, not aged)
Solution B: Potassium stannate(300 ppm) (Comparison, not aged)
Solution C: Solution according to Example Preparation Method 2, (0.12 g)

At ambient temperature, after two weeks, the solutions lost the following percentage of the initial peracetic acid:

| Sample | Peracetic acid lost (% of initial) |
|---|---|
| Solution A | 48.8 |
| Solution B | 48.7 |
| Solution C | 41.8 |

Under the same conditions an unstabilised peracetic acid solution lost 50.1% of its initial peracetic acid.

This demonstrates the effectiveness of the stabilisers described according to the invention at slowing down the loss of peracetic acid, during storage.

We claim:

1. A process for the stabilisation of an aqueous solution of a peroxyacid prepared from a plurality of components by means of the addition of an effective amount of a tin based stabiliser to said solution or to one or more of said components of said solution, wherein said stabiliser is prepared as a coloured solution, which is aged for a time sufficient to obtain its fading before said addition to said peroxyacid solution or to one or more of said components of said solution and to obtain a clear solution having no suspended solids.

2. A process according to claim 1, wherein the peroxyacid comprises a peroxycarboxylic acid.

3. A process according to claim 1 wherein the stabiliser is prepared according to the following steps:
   a) preparing a solution containing a water soluble salt of a stannate with one or more water soluble phosphorus containing salts;
   b) adjusting the pH of the solution to a pH in the range of 9 to 11.5, thereby forming a yellow solution; and
   c) ageing the solution until the yellow coloration fades.

4. A process for the stabilisation of an aqueous solution of a peroxyacid prepared from a plurality of components by means of the addition of an effective amount of a tin based stabiliser to said solution or to one or more of said components of said solution, wherein the stabiliser is prepared according to the steps of:
   a) preparing a solution containing a water soluble salt of a stannate with one or more water solution phosphorus containing salts;
   b) adjusting the pH of the solution to a pH in the range of 9 to 11.5; and
   c) ageing the solution for a period determined by the formula Time=$y(2.3^{(100-T)/10})$ in which time is given in hours, y is the range of from 0.1 to 2, and T is the temperature at which the solution is aged, in Celsius, whereby color of the solution fades and a clear solution having no suspended solids is obtained.

5. A process according to claim 3 or 4, wherein the phosphorus containing salt is selected from one or more of phosphate, condensed linear polyphosphate, or cyclic polyphosphate.

6. A process according to claim 5, wherein the phosphorus containing salt comprises a phosphate.

7. A process according to claim 3 or 4, wherein the pH of the solution is adjusted in the range of 10.9 to 11.1.

8. A process according to claim 3 or 4, wherein the solution ageing of step c) is carried out at an elevated temperature.

9. A process according to claim 4, wherein the amount of tin and phosphorus containing salts is at least 0.005% w/w of the composition.

10. A process according to claim 9, wherein the amount of tin and phosphorus containing salts combined is up to 1% w/w of the solution of the peroxyacid.

11. A process according to claim 1 or 4, wherein the peroxyacid comprises peracetic acid.

12. A process according to claim 1 or 4, wherein the peroxyacid is present at an equilibrium concentration.

13. A process according to claim 1 or 4, wherein the peroxyacid is present at greater than an equilibrium concentration and wherein the tin based stabiliser inhibits the reversion of the peroxyacid into hydrogen peroxide and the corresponding acid.

14. Stabilised aqueous peroxyacid composition prepared from a plurality of components, said composition comprising an effective amount of a tin based stabiliser said stabiliser being prepared as a coloured solution which is aged for a time sufficient to obtain its fading before introduction into the peroxyacid solution or to one or more of said components thereof and to obtain a clear solution having no suspended solids.

15. A composition according to claim 14, wherein the peroxyacid comprises a peroxycarboxylic acid.

16. A composition according to claim 14 wherein the stabiliser is prepared according to the following steps:
   a) preparing a solution containing a water soluble salt of a stannate with one or more water soluble phosphorus containing salts;
   b) adjusting the pH of the solution to a pH in the range of 9 to 11.5, thereby forming a yellow solution; and
   c) ageing the solution until the yellow coloration fades.

17. Stabilised aqueous peroxyacid composition, prepared from a plurality of components, said composition comprising an effective amount of a tin based stabiliser which has been prepared prior to its introduction into the composition or into one or more of said components thereof by steps of:
   a) preparing a solution containing a water soluble salt of a stannate with one or more water solution phosphorus containing salts;
   b) adjusting the pH of the solution to a pH in the range of 9 to 11.5; and
   c) ageing the solution for a period determined by the formula Time=$y(2.3^{(100-T)/10})$ in which time is given in hours, y is the range of from 0.1 to 2, and T is the temperature at which the solution is aged, in Celsius, whereby color of the solution fades and a clear solution having no suspended solids is obtained.

18. A composition according to claim 16 or 17, wherein the phosphorus containing salt is selected from one or more of phosphate, condensed linear polyphosphate, or cyclic polyphosphate.

19. A composition according to claim 18, wherein the phosphorus containing salt comprises a phosphate.

20. A composition according to claim 16 or 17, wherein the pH of the solution is adjusted in the range of 10.9 to 11.1 in step b).

21. A composition according to claim 14 or 17 wherein the stabiliser is aged at an elevated temperature.

22. A composition according to claim 16 or 17, wherein the amount of tin and phosphorus is at least 0.005% w/w of the solution of the peroxyacid.

23. A composition according to claim 16 or 17, wherein the amount of tin and phosphorus is at least 1% w/w of the solution of the peroxyacid.

24. A composition according to claim 14 or 17, wherein the peroxyacid comprises peracetic acid.

25. A composition according to claim 14 or 17, wherein the peroxyacid is present at an equilibrium concentration.

26. A composition according to claim 14 or 17, wherein the peroxyacid is present at greater than an equilibrium concentration and wherein the tin based stabiliser inhibits the reversion of the peroxyacid into hydrogen peroxide and the corresponding acid.

* * * * *